(12) United States Patent
Reavill et al.

(10) Patent No.: US 11,732,841 B2
(45) Date of Patent: Aug. 22, 2023

(54) MEDICAL MULTI-LINK BOOM

(71) Applicant: Stryker Corporation, Kalamazoo, MI (US)

(72) Inventors: James Dulin Reavill, Irving, TX (US); Wojciech Kazimierz Timoszyk, Flower Mound, TX (US); Casey Lee, Dallas, TX (US); David P. Chase, Southlake, TX (US); James K. Alexanderson, Coppell, TX (US); William Lowell Jacques, II, Mount Pleasant, SC (US); Lancer Drake Halcom, Coppell, TX (US); Dustin Ryan Campbell, Fort Worth, TX (US)

(73) Assignee: Stryker Corporation, Kalamazoo, MI (US)

( * ) Notice: Subject to any disclaimer, the term of this patent is extended or adjusted under 35 U.S.C. 154(b) by 506 days.

(21) Appl. No.: 15/902,288

(22) Filed: Feb. 22, 2018

(65) Prior Publication Data
US 2018/0259122 A1    Sep. 13, 2018

Related U.S. Application Data

(60) Provisional application No. 62/467,893, filed on Mar. 7, 2017.

(51) Int. Cl.
*F16M 13/02*     (2006.01)
*A61B 90/35*     (2016.01)
(Continued)

(52) U.S. Cl.
CPC ........... *F16M 13/027* (2013.01); *A61B 90/35* (2016.02); *A61B 90/50* (2016.02); *A61G 12/004* (2013.01);
(Continued)

(58) Field of Classification Search
CPC .. F16M 13/027; F16M 11/08; F16M 11/2014; F16M 2200/00; F16M 2200/021;
(Continued)

(56) References Cited

U.S. PATENT DOCUMENTS 3,858,578 A    1/1975  Milo
4,517,632 A    5/1985  Roos
(Continued)

FOREIGN PATENT DOCUMENTS

DE    19748480 A1    5/1999
EP    0 653 922 A1   5/1995
(Continued)

OTHER PUBLICATIONS

Partial European Search Report issued in Application No. 18159919.2 dated Jun. 26, 2018 (14 pages).
(Continued)

*Primary Examiner* — Jonathan Liu
*Assistant Examiner* — Guang H Guan
(74) *Attorney, Agent, or Firm* — Morrison & Foerster LLP

(57) ABSTRACT

A suspension arm assembly including at least three horizontally aligned members relatively rotatable about each other. Each adjacent pair of members are connected to each other by a joint. At least one conduit extends along the at least three horizontally aligned members, with the at least one conduit being routed horizontally along the horizontally aligned members and not being located within a periphery of the at least three horizontally aligned members.

34 Claims, 15 Drawing Sheets

(51) Int. Cl.
*A61B 90/50* (2016.01)
*H02G 3/04* (2006.01)
*A61G 12/00* (2006.01)
*F16M 11/20* (2006.01)
*F21S 8/06* (2006.01)
*F21V 21/28* (2006.01)
*F21W 131/205* (2006.01)

(52) U.S. Cl.
CPC .......... *F16M 11/2014* (2013.01); *F21S 8/063* (2013.01); *F21V 21/28* (2013.01); *H02G 3/0475* (2013.01); *A61B 2090/508* (2016.02); *F16M 2200/00* (2013.01); *F16M 2200/021* (2013.01); *F16M 2200/068* (2013.01); *F21W 2131/205* (2013.01)

(58) Field of Classification Search
CPC .. F16M 2200/068; A61B 90/35; A61B 90/50; A61B 6/0464; A61B 6/4464; A61G 12/004; H02G 3/0475; F21S 8/063; F21V 21/28; F21W 2131/205
See application file for complete search history.

(56) References Cited

U.S. PATENT DOCUMENTS

| | | | | |
|---|---|---|---|---|
| 4,855,560 A * | 8/1989 | Sonoda | ............. | B23K 11/3018 219/86.25 |
| 4,998,702 A | 3/1991 | Reuter et al. | | |
| 5,014,693 A | 5/1991 | Wright, II et al. | | |
| 5,025,126 A | 6/1991 | Hansen | | |
| 6,095,468 A * | 8/2000 | Chirico | ............. | F16M 11/2014 248/125.7 |
| 6,246,200 B1 * | 6/2001 | Blumenkranz | ........ | B25J 9/1689 128/DIG. 7 |
| 6,569,084 B1 * | 5/2003 | Mizuno | ............. | A61B 1/00149 248/325 |
| 6,601,811 B1 * | 8/2003 | Van Lieshout | ........ | F16M 11/08 248/282.1 |
| 7,240,477 B1 * | 7/2007 | Dunfee | ............. | F16G 13/16 248/49 |
| 8,226,072 B2 * | 7/2012 | Murayama | ........... | B25J 19/0004 269/55 |
| 8,336,839 B2 * | 12/2012 | Boccoleri | ............ | A61G 12/004 248/276.1 |
| 8,360,408 B2 * | 1/2013 | Bereznicki | ........... | B25J 19/0004 187/343 |
| 9,857,024 B1 * | 1/2018 | Culpepper | ........... | F16M 13/027 |
| 11,123,249 B2 * | 9/2021 | Halcom | ............... | F16M 13/027 |
| 2008/0132755 A1 | 6/2008 | Kanazawa | | |
| 2010/0181440 A1 | 7/2010 | Larsen et al. | | |
| 2010/0258694 A1 | 10/2010 | Steger | | |
| 2011/0121141 A1 | 5/2011 | Tatsuta et al. | | |
| 2013/0247919 A1 | 9/2013 | Chauvette et al. | | |
| 2013/0330043 A1 * | 12/2013 | Goldsmith | ........... | G02B 6/4452 385/70 |
| 2015/0184779 A1 * | 7/2015 | Timoszyk | ............... | A61B 90/30 285/282 |
| 2016/0091117 A1 | 3/2016 | Boccoleri et al. | | |
| 2016/0120720 A1 * | 5/2016 | Hirsch | ................. | A61G 13/101 5/503.1 |
| 2016/0296297 A1 * | 10/2016 | Perplies | ................. | F16M 11/26 |
| 2017/0357361 A1 * | 12/2017 | Hong | .................. | G01K 13/028 |
| 2018/0017736 A1 | 1/2018 | Boccoleri et al. | | |
| 2018/0206936 A1 | 7/2018 | Oginski et al. | | |
| 2018/0259122 A1 * | 9/2018 | Reavill | .................... | F21V 21/28 |
| 2019/0336373 A1 * | 11/2019 | Halcom | ............... | A61G 12/005 |

FOREIGN PATENT DOCUMENTS

| | | |
|---|---|---|
| EP | 0 928 393 A1 | 7/1999 |
| EP | 1 922 975 A1 | 5/2008 |
| FR | 2801369 A1 | 5/2001 |
| JP | 7-241300 A | 9/1995 |
| WO | 94/03113 A1 | 2/1994 |
| WO | WO 94/03113 A1 | 2/1994 |
| WO | 98/13643 A1 | 4/1998 |
| WO | WO 98/13643 A1 | 4/1998 |
| WO | 2008/042346 A2 | 4/2008 |
| WO | WO 2016/015820 A1 | 2/2016 |

OTHER PUBLICATIONS

Australian Examination Report issued in AU 2018201287 dated Aug. 14, 2018 (4 pages).
Extended European Search Report dated Nov. 7, 2018, directed to EP Application No. 18159919.2; 16 pages.
Notice of Acceptance for Patent Application dated Dec. 13, 2018, directed to AU Application No. 2018201287; 3 pages.
Office Action dated Feb. 12, 2020, directed to CA Application No. 2,996,550; 4 pages.
Office Action dated May 23, 2019, directed to CA Application No. 2,996,550; 3 pages.
Office Action dated May 31, 2022, directed to EP Application No. 18 159 919.2; 5 pages.

* cited by examiner

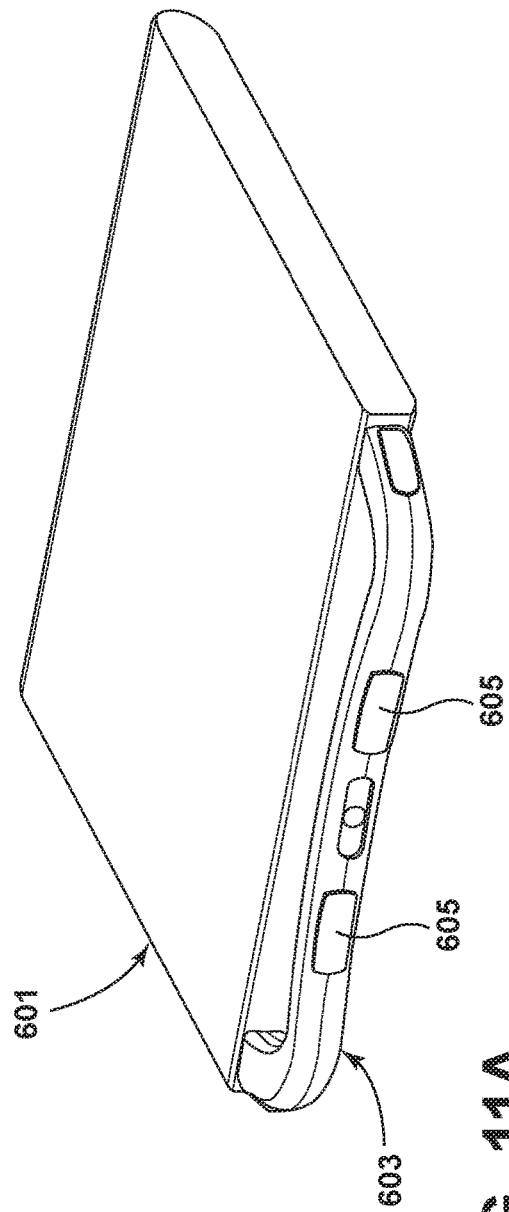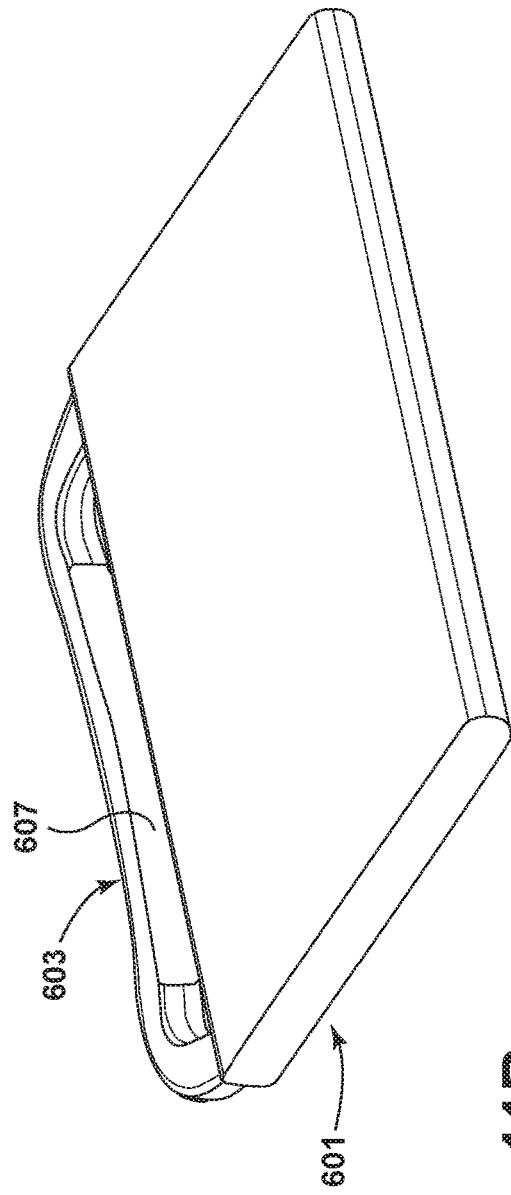

MEDICAL MULTI-LINK BOOM

CROSS REFERENCE TO RELATED APPLICATION

This claims the benefit of U.S. Provisional Application Ser. No. 62/467,893, filed Mar. 7, 2017.

FIELD OF THE INVENTION

The present invention relates to a suspension arm assembly, and in particular to a multi-link boom.

BACKGROUND OF THE INVENTION

Surgical service heads are configured to provide outlets for electricity, data, gases and/or fluids for use by the medical personnel in a medical room and/or to assist the medical personnel in the room to perform various functions. Moreover, surgical lights have been used in operating rooms to provide increased light to a specific area of the room. For example, the surgical light can be positioned within an operating room and can provide increased light to a specific area of a person being operated on within the operating room. Furthermore, surgical devices, such as speakers, joysticks, keyboards and cameras, have been used in operating rooms to provide information to a surgeon or other person in the operating room (e.g., images from a camera or patient vital information).

It is desired to have an easier way to position the surgical devices.

SUMMARY OF THE INVENTION

The present invention, according to one aspect, is directed to a suspension arm assembly including at least three horizontally aligned members relatively rotatable about each other, with each adjacent pair of members being connected to each other by a joint and with each of the at least three horizontally aligned members defining a load bearing periphery, and at least one conduit extending along the at least three horizontally aligned members, with the at least one conduit not being located within the load bearing periphery of the at least three horizontally aligned members.

Yet another aspect of the present invention is to provide a medical suspension arm assembly including a ceiling attachment member for connecting the medical suspension arm assembly to a ceiling, at least three horizontally aligned members relatively rotatable about each other, with each adjacent pair of members being connected to each other by a joint and with each of the at least three horizontally aligned members defining a load bearing periphery, a medical device for providing medical services or information, and at least one conduit extending along the ceiling attachment member, with the at least three horizontally aligned members and to the medical device, the at least one conduit not being located within the load bearing periphery of the at least three horizontally aligned members.

Another aspect of the present invention is to provide a medical suspension arm assembly including an attachment member for connecting the medical suspension arm assembly to a support structure, at least three horizontally aligned members relatively rotatable about each other, with each adjacent pair of members being connected to each other by a joint and with each of the at least three horizontally aligned members having an arm horizontal length smaller than 25% of a total horizontal length of all of the horizontally aligned members, a medical device for providing medical services or information, and at least one conduit extending along the ceiling attachment member, with the at least three horizontally aligned members and to the medical device, the at least one conduit being routed horizontally and not vertically between adjacent pairs of the horizontally aligned members.

Yet another aspect of the present invention is to provide a medical suspension arm assembly. The medical suspension arm assembly includes an attachment member for connecting the medical suspension arm assembly to a support structure, at least three horizontally aligned members relatively rotatable about each other, with each adjacent pair of members being connected to each other by a joint, a medical device for providing medical services or information, and at least one conduit extending along the attachment member, the at least three horizontally aligned members and to the medical device. Each joint has a brake system for selectively preventing movement of adjacent ones of the at least three horizontally aligned members about the joint, with each brake system being located outside a periphery of an associated one of the at least three horizontally aligned members.

Another aspect of the present invention is to provide a method of using a suspension arm assembly including providing at least three horizontally aligned members relatively rotatable about each other, connecting each adjacent pair of members to each other by a joint, with each of the at least three horizontally aligned members defining a load bearing periphery, and extending at least one conduit along the at least three horizontally aligned members, with the at least one conduit not being located within the load bearing periphery of the at least three horizontally aligned members.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

FIG. 11A is a front perspective view of a shelf of the suspension arm assembly of the present invention illustrating a first method of moving the suspension arm assembly.

FIG. 11B is a rear perspective view of a shelf of the suspension arm assembly of the present invention illustrating the first method of moving the suspension arm assembly.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

Figure 1A:
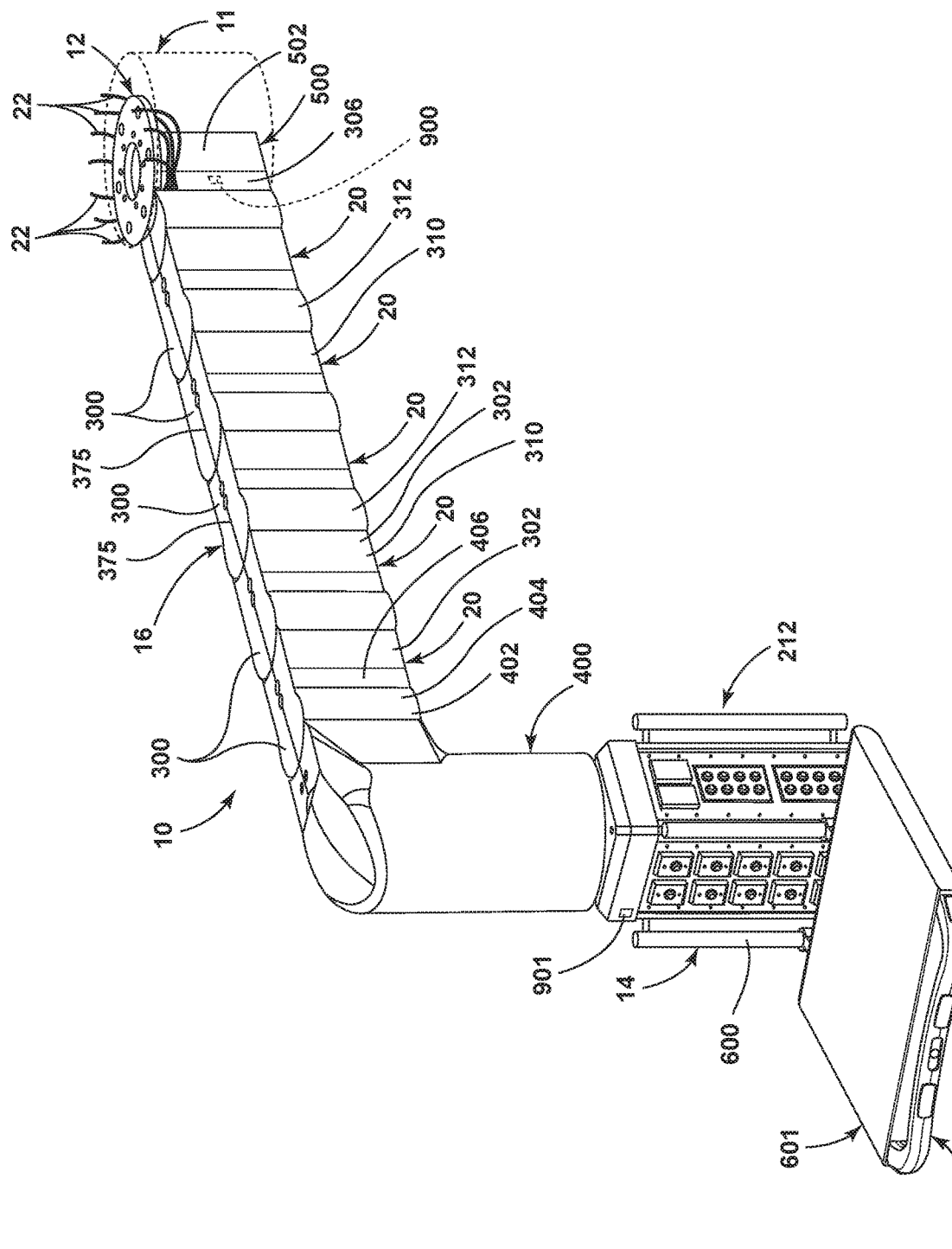
FIG. 1A illustrates a perspective view of a first embodiment of a suspension arm assembly having a multi-link boom including a plurality of boom shells according to the present invention and including a service head connected thereto.

The reference number 10 (FIG. 1A) generally designates a suspension arm assembly of the present invention. The suspension arm assembly 10 includes a ceiling connector 12, a service head 14 and a multi-link boom 16 between the ceiling connector 12 and the service head 14. The multi-link boom 16 includes a plurality of boom arms 18 (see FIGS. 2-4, 7 and 8) each covered by a boom arm shell 20. Each of the boom arms 18 can rotate relative to each other to provide for multiple end locations for the service head 14. The illustrated suspension arm assembly 10 is configured to be positioned within a room (e.g., an operating room or a patient care area) and, in the illustrated embodiment, includes the service head 14, which is configured to provide outlets for electricity, data, gases and/or fluids for use by the medical personnel in the room and/or to assist the medical personnel in the room in performing various functions. It is contemplated that other items (e.g., a surgical light 14a as illustrated in FIG. 1C, a display monitor, dual displays, cameras, microphones, etc.) can be located at the end of the suspension arm assembly 10 instead of the service head 14.

In the illustrated example, the suspension arm assembly 10 is connected to a ceiling and supports the service head 14 above a support surface, such as a floor. The suspension arm assembly 10 includes the ceiling connector 12, the multi-link boom 16 and the service head 14. While the multi-link boom 16 is illustrated as having five boom arms 18, it is contemplated that the suspension arm assembly 10 could have any number of boom arms 18. Furthermore, while the suspension arm assembly 10 includes the ceiling connector 12 for connecting the suspension arm assembly 10 to a ceiling, it is contemplated that the ceiling connector 12 could be used to connect the suspension arm assembly 10 to any structure (fixed or movable) above a support surface, such as a floor, wall or pedestal. Moreover, as discussed in more detail below, the multi-link boom 16 can include a single, flexible boom sleeve 20a (see FIG. 1B) functioning as a bellows and/or is elastic at joints instead of a plurality of boom arm shells 20 covering the multi-link boom 16. The illustrated suspension arm assembly 10 includes conduits 22 for electricity, power, video, data, gases and/or liquids routed through the ceiling connector 12 and the boom arms 18 for the service head 14 (see FIG. 2).

Figure 2:
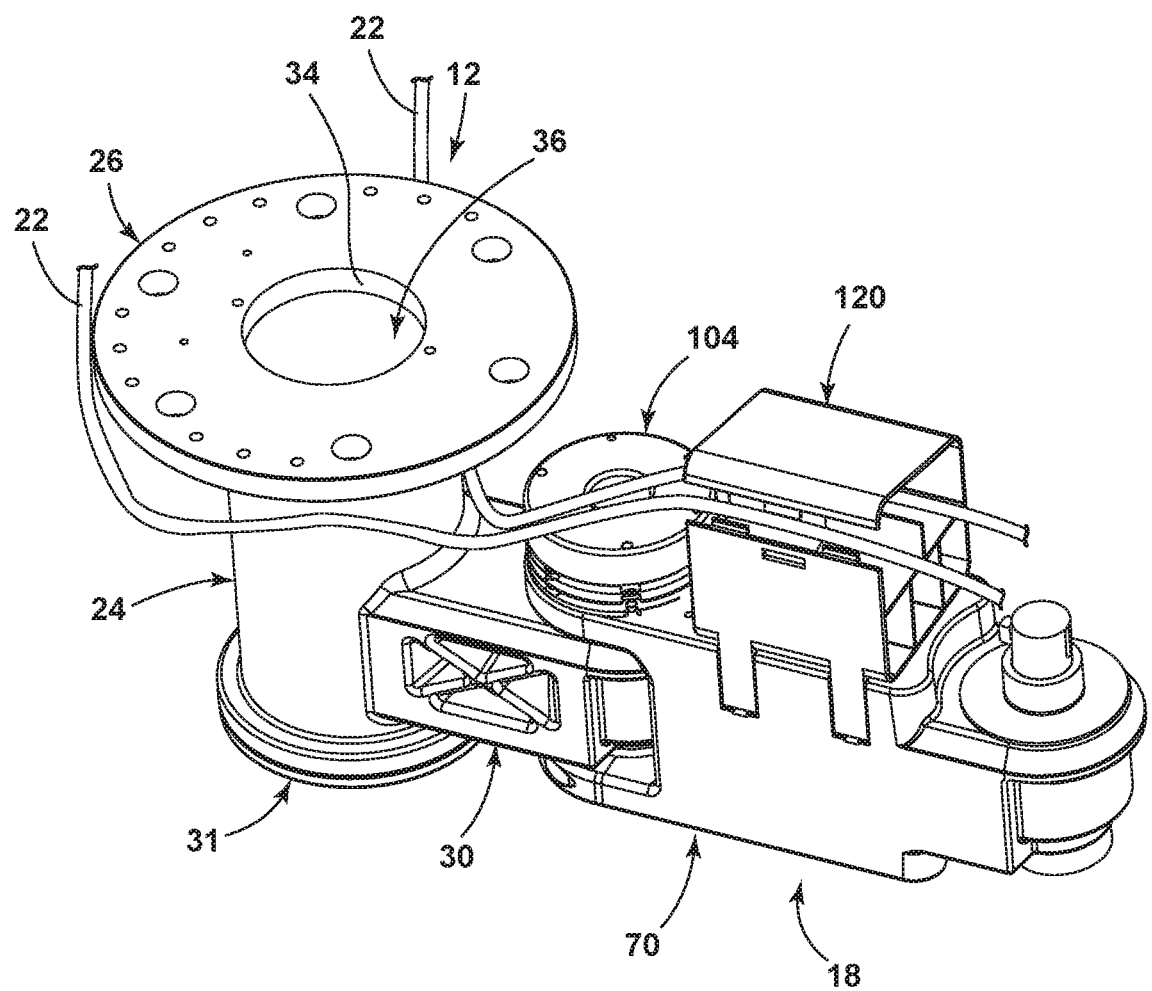
FIG. 2 is a perspective view of a ceiling connector and first boom arm of the multi-link boom according to the present invention.

The illustrated ceiling connector 12 connects a first one of the boom arms 18 of the multi-link boom 16 to a support as illustrated in FIG. 2. The ceiling connector 12 (FIGS. 2, 5 and 6) includes a center cylinder 24, a top plate 26, a bottom rim 31, a side connection arm 30 and a pivot pin 32. The side connection arm 30 has the first one of the boom arms 18 connected thereto for rotation about the pivot pin 32. The top plate 26 is configured to connect the ceiling connector 12, and thereby the entire suspension arm assembly 10, to a support. The top plate 26 can be stationary and fixed to the support or can be configured to pivot about the support. If pivotable, it is contemplated that the top plate 26 can have a limited range of motion relative to the support (e.g., by using stops). If the conduits 22 only carry electricity, power, video or data, it is contemplated that the ceiling connector 12 (or adjacent structure) could have infinite rotation relative to the support by housing a slip ring or a fiber optic rotary joint therein (e.g., in the center cylinder 24), such as those disclosed in U.S. Patent Application Publication No. 2016/0091117 entitled FIBER OPTIC SLIP RING ROTARY JOINT FOR SUSPENSION ARM or in U.S. Patent Application No. 62/361,301 entitled SEPARABLE INFINITE ROTATION FIBER OPTIC AND SLIP RING ROTARY JOINT FOR SUSPENSION ARM, the entire contents of both of which are incorporated herein by reference. The center cylinder 24 is connected to a bottom of the top plate 26 and the bottom rim 31 is connected to a bottom of the center cylinder 24. The center cylinder 24 includes a bottom enclosure at the bottom rim 31 for enclosing a bottom of the center cylinder 24.

In the illustrated example, the ceiling connector 12 includes the side connection arm 30 for connecting the boom arms 18 to the support for the suspension arm assembly 10. The center cylinder 24 is connected to a bottom of the top plate 26 and the side connection arm 30 extends laterally from an outside surface 28 of the center cylinder 24 (see FIG. 6). As shown in FIG. 2, the conduits 22 extend around the top plate 26 and through a top wire routing holder 120 as discussed in more detail below. The pivot pin 32 allows the adjacent boom arm 18 to rotate about the ceiling connector 12. The side connection arm 30 includes a central block portion 40 that can include a plurality of cutouts 42 therethrough or therein to reduce weight of the side connection arm 30. The side connection arm 30 has an arcuate free end 44 having a plurality of vertical downwardly facing steps 46 becoming smaller going downward. The steps 46 allow for easy connection of the boom arm 18 to the ceiling connector 12 as discussed in more detail below.

Figure 5:
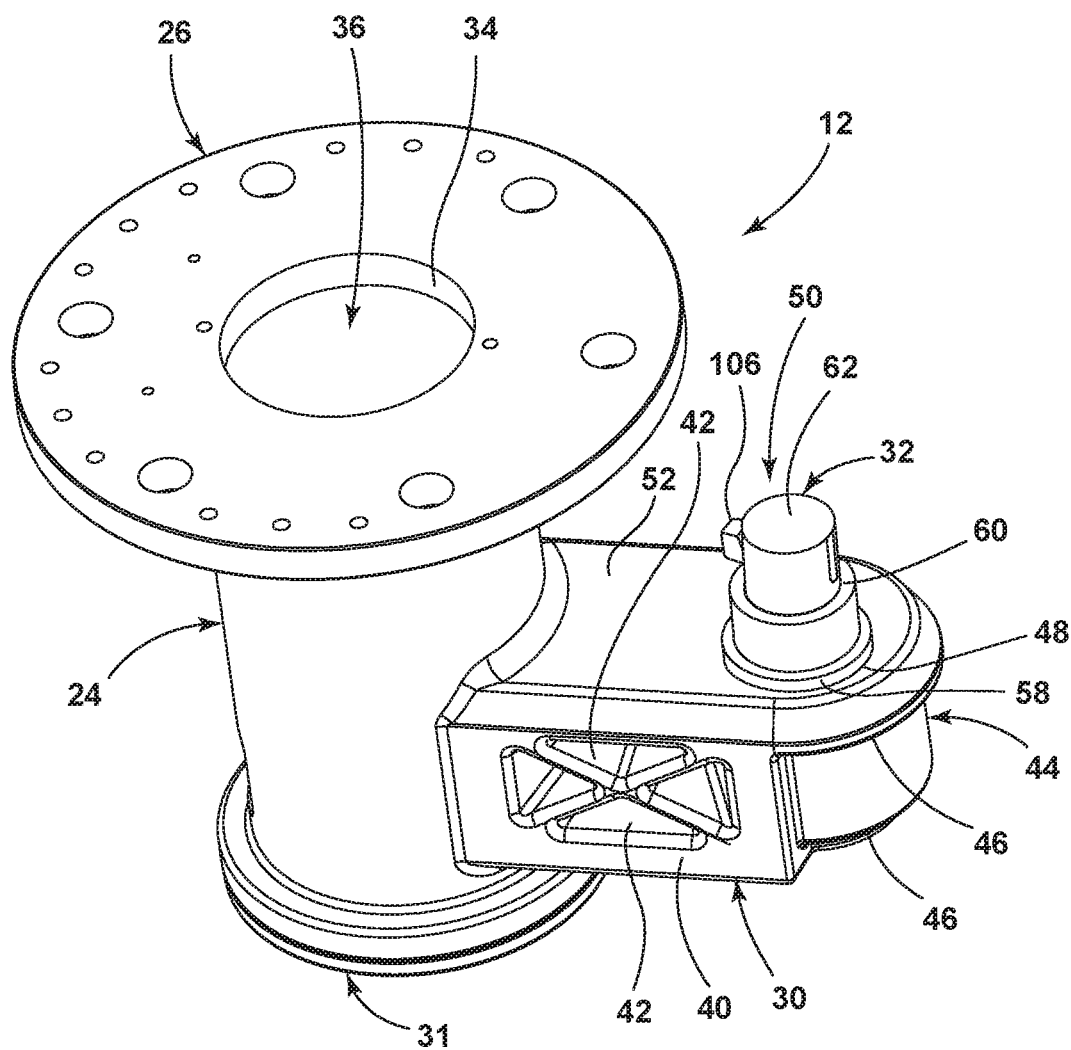
FIG. 5 is a perspective view of the ceiling connector according to the present invention.
Figure 6:
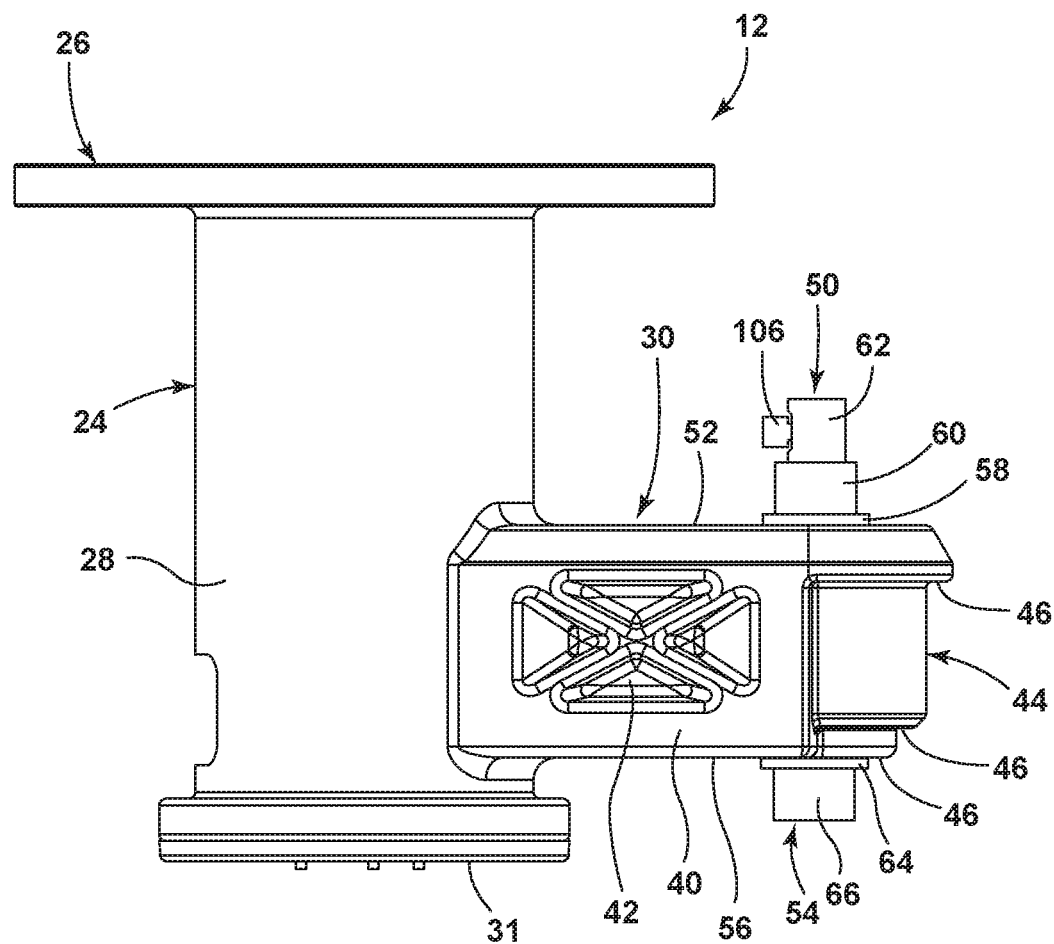
FIG. 6 is a side view of the ceiling connector according to the present invention.

The illustrated pivot pin 32 is located in a vertical aperture 48 adjacent the arcuate free end 44 of the side connection arm 30. As illustrated in FIGS. 5 and 6, the pivot pin 32 includes a top portion 50 extending upwardly from a top surface 52 of the central block portion 40 of the side connection arm 30 and a bottom portion 54 extending downwardly from a bottom surface 56 of the central block portion 40 of the side connection arm 30. The top portion 50 includes a plurality of aligned cylinders including a lower cylinder 58, a middle cylinder 60 and an upper cylinder 62. The middle cylinder 60 extends into the central block portion 40 and includes at least one internal step supported on ledges within the vertical aperture 48 for supporting the pivot pin 32 within the central block portion 40. The bottom portion 54 of the pivot pin 32 includes a plurality of aligned cylinders including a top cylinder 64 and a bottom cylinder 66. It is contemplated that the top portion 50 and the bottom portion 54 of the pivot pin 32 can be integral or separate.

In the illustrated example, the boom arm 18 adjacent the ceiling connector 12 pivots about the pivot pin 32. The boom arm 18 (FIGS. 7 and 8) includes a hollow structural main portion 70 having a central body 72, a proximal connection portion 74 and a boom arm side connection arm 76. The structural main portion 70 is hollow, but comprises the load bearing portion of the boom arm 18 for supporting the load (e.g., the weight of the arms distal to the present arm 18 and the service head 14) at the end of the multi-link boom 16. The central body 72 has a substantially rectangular cross-sectional shape with a pair of side walls 78, a top wall 80 and a bottom wall 82.

The illustrated proximal connection portion 74 of the structural main portion 70 of the first boom arm 18 is located adjacent the ceiling connector 12 and connects the first boom arm 18 to the ceiling connector 12. The proximal connection portion 74 includes a proximal side top connection plate 84 extending laterally from the top wall 80 of the central body 72 and a proximal side bottom connection plate 86 extending laterally from the bottom wall 82 of the central body 72. The proximal side top connection plate 84 includes a top pin opening for accepting the middle cylinder 60 of the top portion 50 of the pivot pin 32 of the ceiling connector 12 therein. A top bushing can be located within the top pin opening between a peripheral wall thereof and a top bearing race 88 surrounding the middle cylinder 60 of the top portion 50 of the pivot pin 32 for allowing the first boom arm 18 to easily rotate about the pivot pin 32. A top bearing race 88 is shown about a pivot pin 32' of the first boom arm 18 in FIGS. 7 and 8, which is identical to the pivot pin 32 of the ceiling connector 12 as discussed in more detail below. During assembly, the top portion 50 of the pivot pin 32 of the ceiling connector 12 is inserted into the top pin opening of the proximal side top connection plate 84 and the structural main portion 70 is rotated clockwise as viewed in the orientation of FIG. 2 to connect the ceiling connector 12 to the first boom arm 18. The steps 46 of the arcuate free end 44 of the side connection arm 30 of the ceiling connector 12 provide clearance for the proximal side bottom connection plate 86 to be positioned under the side connection arm 30 of the ceiling connector 12.

In the illustrated example, the proximal side bottom connection plate 86 includes a pair of fingers 90 and a C-shaped lock flange 92 connected to ends 94 of the fingers 90. During connection of the boom arm 18 to the ceiling connector 12, the C-shaped lock flange 92 is not connected to the fingers 90, thereby allowing the bottom portion 54 of the pivot pin 32 to be received within an arcuate surface 96 between the fingers 90. A bottom bushing 101 and a bottom bearing race 98 are positioned on the bottom portion 54 of the pivot pin 32 for allowing the first boom arm 18 to easily rotate about the pivot pin 32. A bottom bearing race 98 is shown about a pivot pin 32' of the first boom arm 18 in FIGS. 7 and 8. After the bottom bushing 101, the bottom bearing race 98 and the bottom portion 54 of the pivot pin 32 are received within the arcuate surface 96 between the fingers 90, ends 100 of the C-shaped lock flange 92 are positioned against the ends 94 of the fingers 90 and fasteners are inserted into openings 102 in the C-shaped lock flange 92 and into the fingers 90 to form the proximal side bottom connection plate 86 and thereby fix the first boom arm 18 to the ceiling connector 12.

Figure 7:
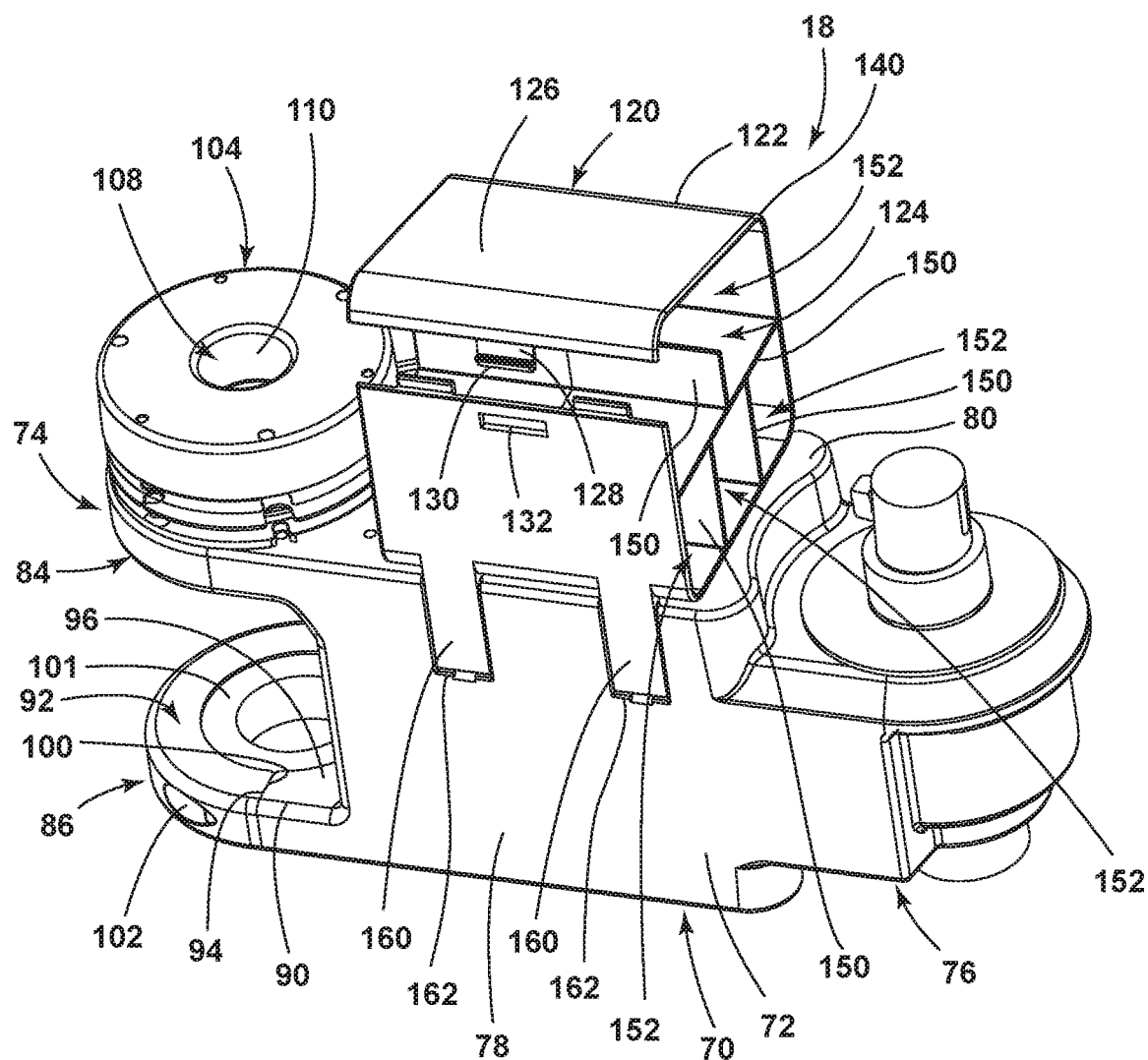
FIG. 7 is a perspective view of the boom arm according to the present invention.
Figure 8:
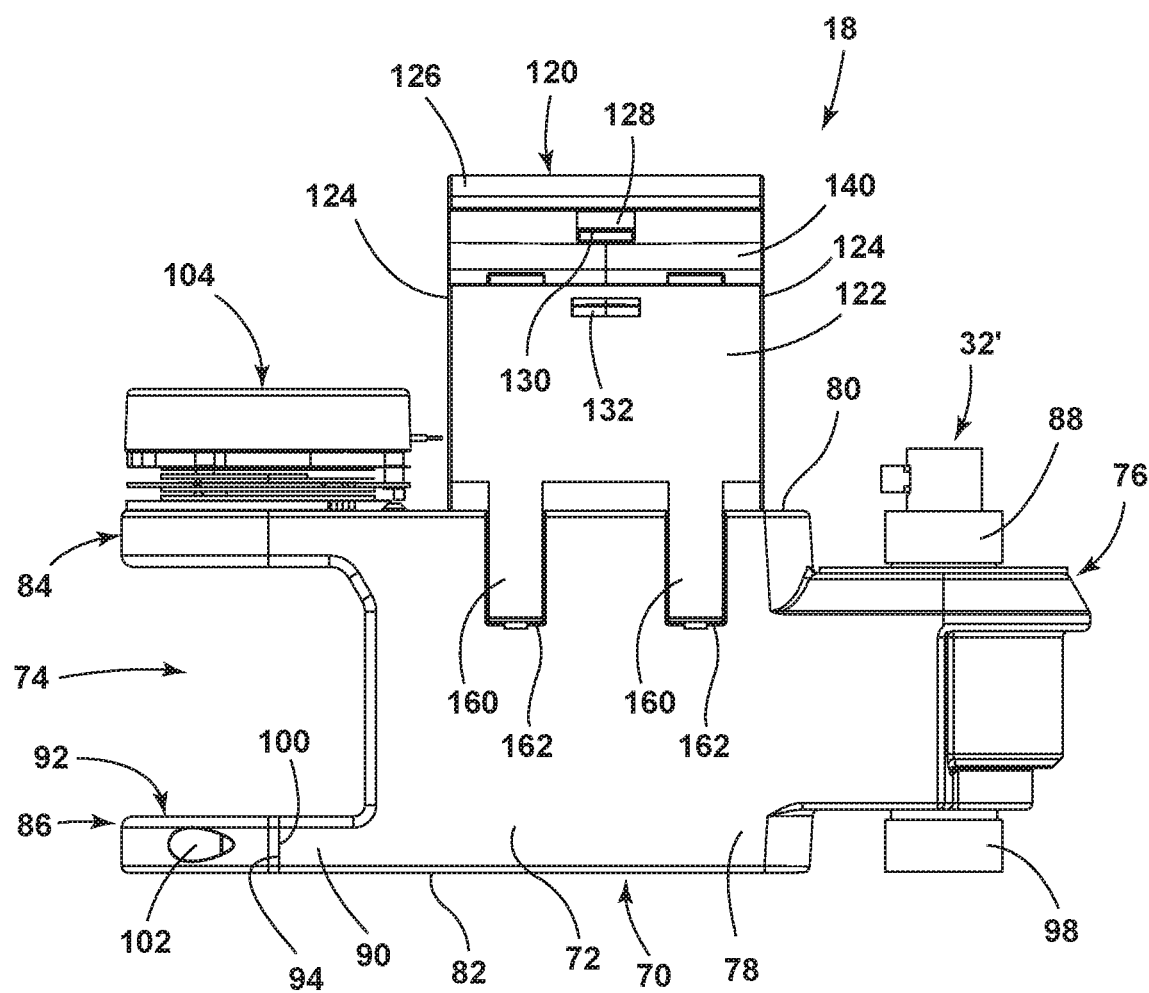
FIG. 8 is a side view of the boom arm according to the present invention.

The illustrated boom arm 18 includes a brake system 104 for selectively preventing rotation of the boom arm 18 adjacent the ceiling connector 12 about the pivot pin 32. In the illustrated example, the pivot pin 32 is fixed in position in the vertical aperture 48 of the ceiling connector 12 and selectively locked in position relative to the adjacent boom arm 18 by the brake system 104. However, it is contemplated that the pivot pin 32 could be fixed in position relative to the boom arm 18 and selectively locked in position relative to the ceiling connector 12 by the brake system 104. As illustrated in FIG. 7, the brake system 104 is disc-shaped and includes a central opening 108. The upper cylinder 62 of the top portion 50 of the pivot pin 32 is received within the central opening 108 of the brake system 104. As shown in FIG. 6, the upper cylinder 62 of the top portion 50 includes a laterally extending lock pin 106. The lock pin 106 is located within a circular run 110 outside the central opening 108 of the brake system 104. The brake system 104 is configured to selectively stop movement of the lock pin 106, thereby preventing rotation of the boom arm 18 about the pivot pin 32 and locking the boom arm 18 is position relative to the boom arm 18.

Figure 3:
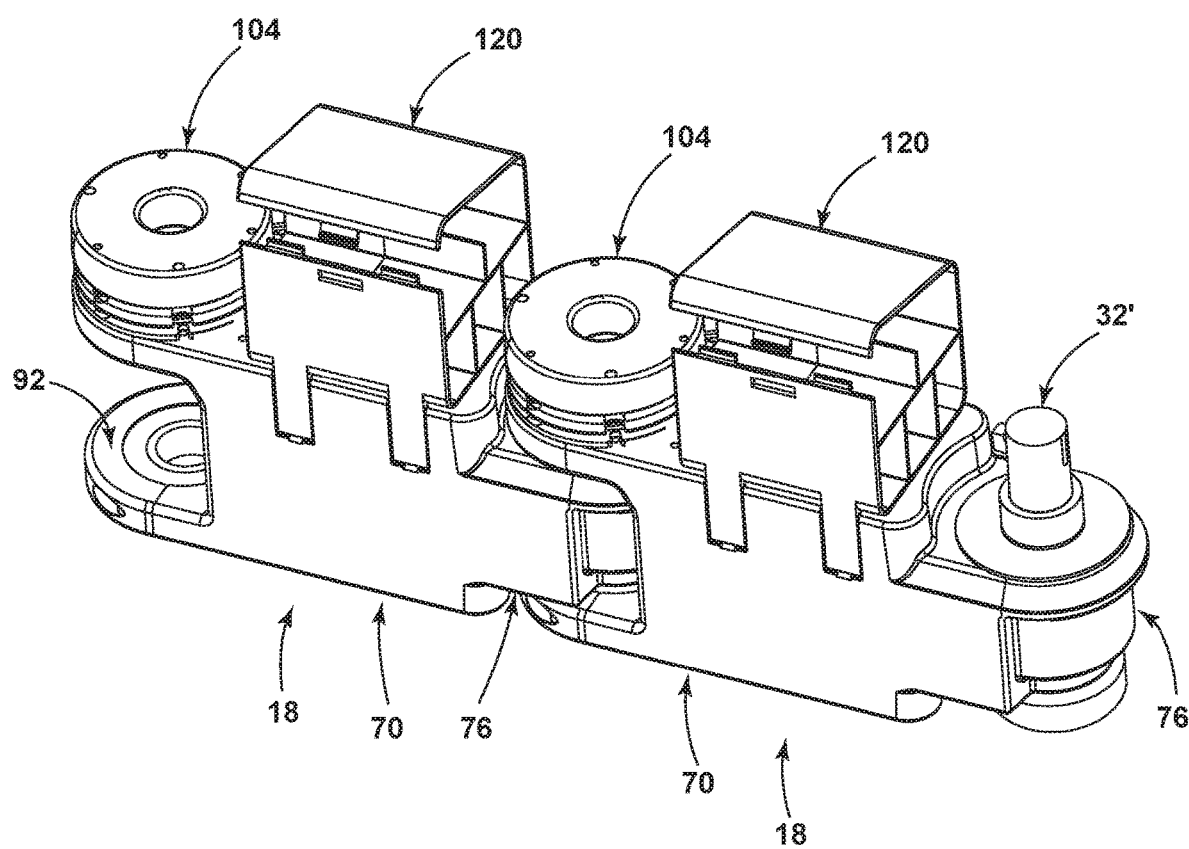
FIG. 3 is a perspective view of a pair of boom arms of the multi-link boom according to the present invention.

In the illustrated example, the boom arm side connection arm 76 of the boom arm 18 is identical to the side connection arm 30 of the ceiling connector 12 and includes the pivot pin 32', which is identical to the pivot pin 32, such that a detailed discussion of the boom arm side connection arm 76, the pivot pin 32' and connection thereof to an adjacent boom arm 18 is not necessary. The boom arm side connection arm 76 of the boom arm 18 allows the boom arm 18 to be connected to an adjacent boom arm 18 as illustrated in FIG. 3. Each boom arm 18 forming the multi-link boom 16 is either connected to the ceiling connector 12 or an adjacent boom arm 18. Furthermore, all boom arms 18 except for the first boom arm 18 connected to the ceiling connector 12 and the last boom arm 18 connected to the service head 14 are flanked by a pair of boom arms 18.

The illustrated conduits 22 of the suspension arm assembly 10 are supported by the boom arms 18, but are not located within (i.e., are outside of) the load bearing portion of the boom arm 18 comprising the structural main portion 70. Therefore, the conduits 22 have a larger range of motion for bending to prevent breakage of the conduits 22 and also allow for easier routing of and access to the wires in the boom arms 18. As illustrated in FIG. 2, the conduits 22 are routed through a top wire routing holder 120. The top wire routing holder 120 includes a rectangular shell 122 having open ends 124. The shell 122 includes a top door 126 shown partially open in FIGS. 2-4, 7 and 8. The top door 126 includes a latch 128 having a hook 130 configured to be inserted into a hole 132 to close the top door 126 and form a periphery about the conduits 22. It is contemplated that the top door 126 can be pivotable about a living hinge 140 for allowing the top door 126 to rotate relative to the rest of the rectangular shell 122. The top wire routing holder 120 can include a plurality of partitions 150 forming dividing cells 152 for assisting in routing the conduits 22 and keeping the conduits 22 separate from other conduits 22 within the top wire routing holder 120. The top wire routing holder 120 can include a pair of resilient legs 160 that snap fit into slots 162 on each of the side walls 78 of the central body 72 to connect the top wire routing holder 120 to the structural main portion 70 of the boom arms 18.

Figure 4:
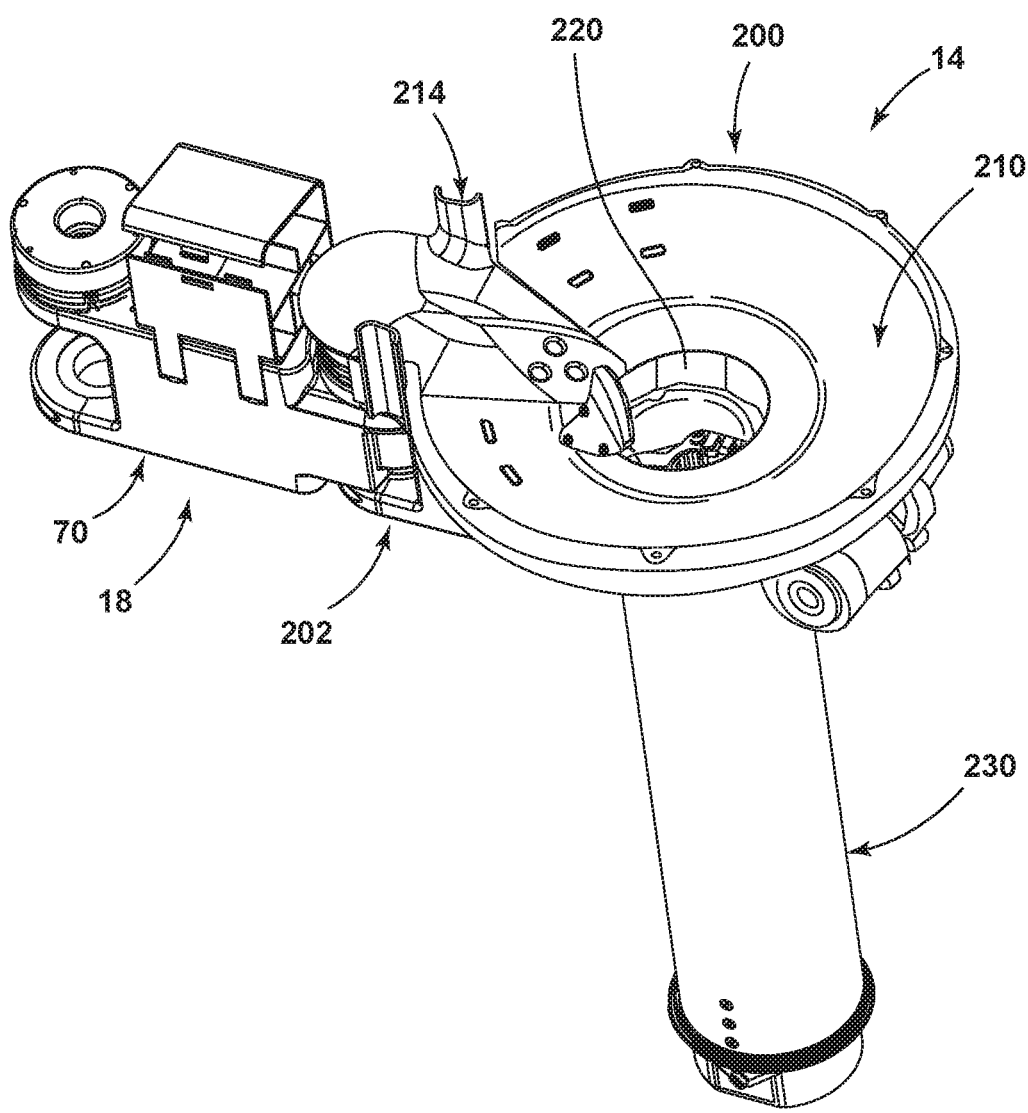
FIG. 4 is a perspective view of an end boom arm of the multi-link boom according to the present invention connected to a service head connector.

In the illustrated example, the last boom arm 18 is connected to the service head 14. As illustrated in FIG. 4, the service head 14 can include a boom connecting assembly 200 for connecting the multi-link boom 16 to the service head 14. The boom connecting assembly 200 can include a pivot connection 202 identical to the proximal connection portion 74 of the boom arms 18. The boom connecting assembly 200 connects to the pivot pin 32' of the adjacent boom arm 18 in the same manner that adjacent boom arms 18 are connected together such that additional discussion on the connection is not necessary. The boom connecting assembly 200 also includes a brake system 104 for breaking rotation of the service head 14 relative to the multi-link boom 16. The boom connecting assembly 200 also includes a funnel 210 for routing and accommodating the conduits 22 from the multi-link boom 16 to a drop tube (not shown) and a service head main portion 212 (see FIG. 1) along with accommodating the conduits to allow for rotation of the service head 14 and vertical movement of the service head 14. The conduits 22 are routed out of the top wire routing holder 120 of the last boom arm 18, through a collection gate 214 at a top edge of the funnel 210 and into a bottom tube 220 of the funnel 210. The conduits 22 are then routed through a pair of telescoping tubes 230 connected to the service head mean portion 212. The pair of telescoping tubes 230 allow for the pair of telescoping tubes 230 to be lowered and raised.

Figure 9:
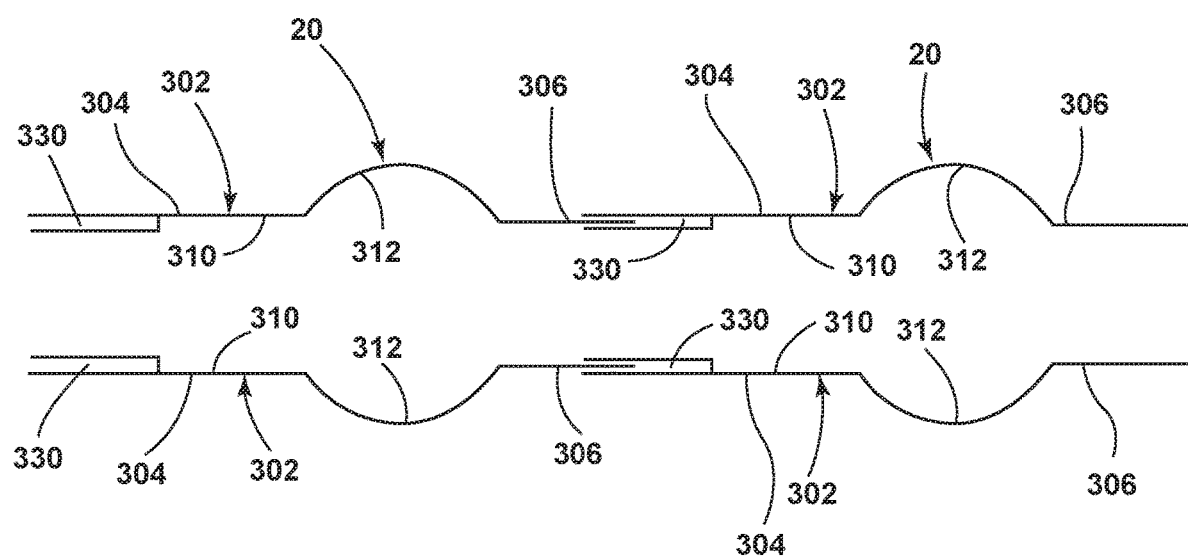
FIG. 9 is a schematic cross-sectional view of a pair of boom arm shells according to the present invention.

In the illustrated example, each of the boom arms 18 includes the boom arm shell 20 thereon. The boom arm shells 20 allow for the multi-link boom 16 to be covered and allow for each boom arm 18 to rotate relative to an adjacent boom arm 18, the ceiling connector 12 or the service head 14. Each boom arm shell 20 includes a bottom surface, a top surface 300 and a pair of side surfaces 302. FIG. 9 illustrates a pair of boom arm shells 20 and the manner in which adjacent boom arm shells 20 move relative to each other and continue to cover the boom arms 18. Each side surface 302 of the boom arm shell 20 includes a rigid portion 304 and a flexible portion 306. The rigid portion 304 of each side surface 302 of the boom arm shell 20 covers a side of the boom arm 18 and includes a straight portion 310 and an arcuate portion 312. The arcuate portion 312 surrounds the pivot pin 32, 32' at the proximal side of the boom arm 18 (i.e., the side nearest the ceiling connector 12). Each straight portion 310 of the rigid portion 304 of the side surface 302 includes a pocket 330 accepting the flexible portion 306 of the side surface 302 of the adjacent boom arm shell 20. As the boom arms 18 rotate relative to each other, the flexible portions 306 slide further into and out of the pockets 330. The flexible portions 306 are sufficiently long to always cover the boom arms 18. It is contemplated that the boom arm shells 20 could include a top split 375 with associated connector to allow the boom arm shells 20 to be positioned over the boom arms 18 by splitting the boom arm shells 20 at the top split 375, wrapping the boom arm shells 20 about the boom arms 18 and then connecting the boom arm shells 20 at the top split 375. The top split 375 may also be opened to allow easy access to the conduits 22 for placement and/or service.

Figure 1B:
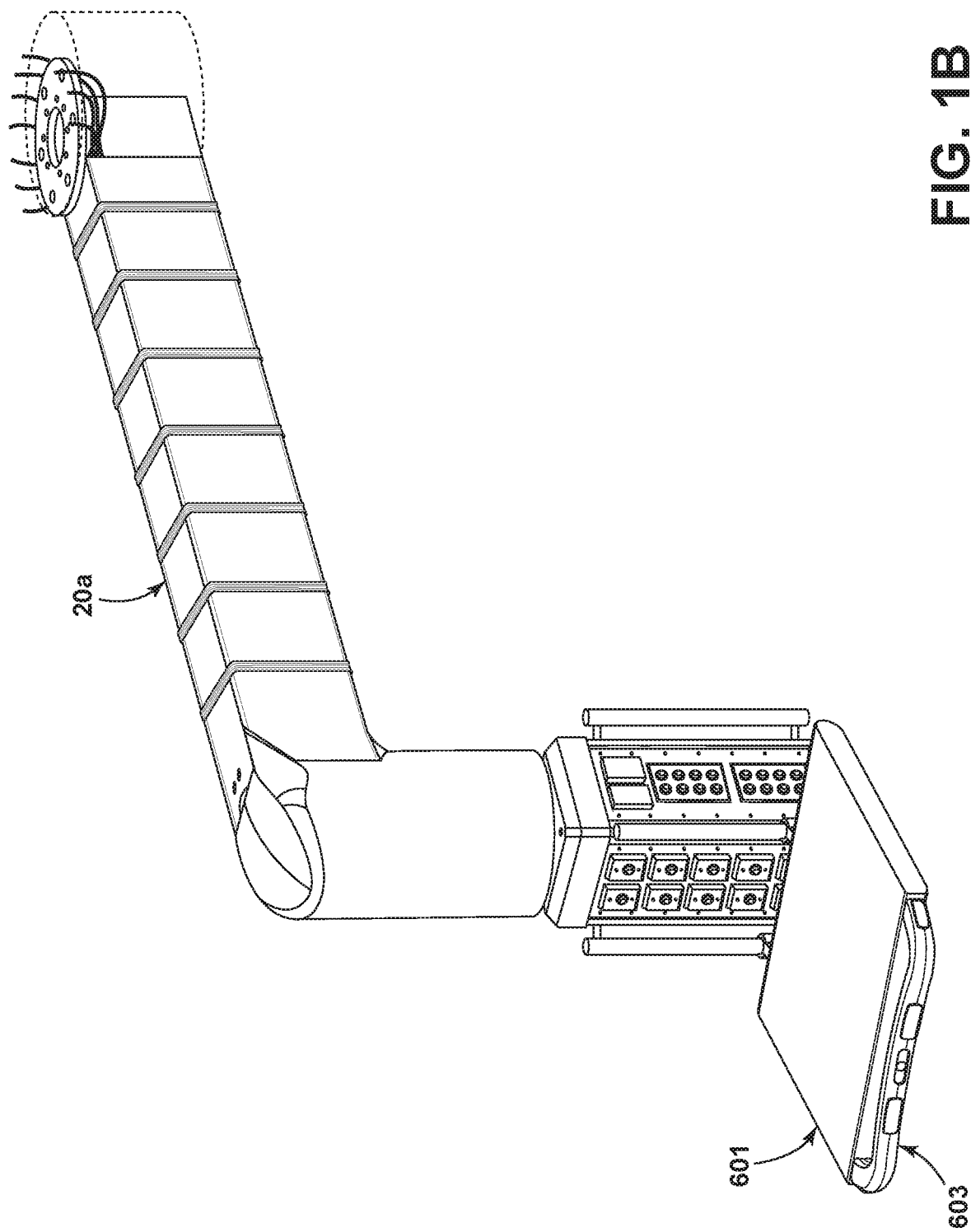
FIG. 1B illustrates a perspective view of a second embodiment of a suspension arm assembly having the multi-link boom including a single boom sleeve according to the present invention and including the service head connected thereto.
Figure 1C:
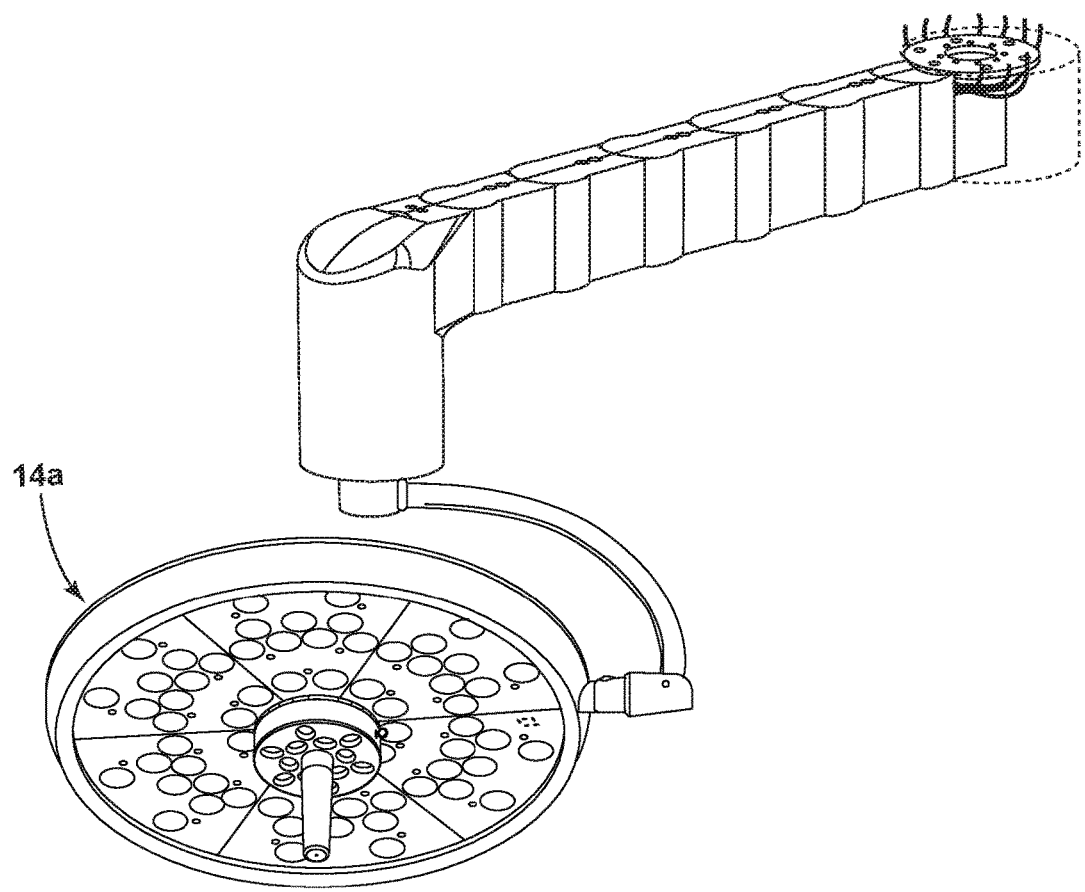
FIG. 1C illustrates a perspective view of a third embodiment of a suspension arm assembly having the multi-link boom including the plurality of boom shells according to the present invention and including a surgical light connected thereto.

As illustrated in FIG. 1, a service head cover 400 includes a pair of side surfaces 402 with an arcuate portion 404 covering the pivot pin 32' of the adjacent boom arm 18 and a flexible portion 406 received within the pocket 330 of the adjacent boom arm shell 20. Likewise, a ceiling connector cover 500 includes a rigid side 502 with a pocket receiving the flexible portion 306 of the adjacent boom arm shell 20. In FIG. 1B, the single boom sleeve 20a is a flexible tube with bellows or elastic material at seams thereof that covers all of the boom arms 18 (instead of the shells).

While a particular braking assembly has been illustrated to allow the boom arms 18 to brake in a selected rotated position relative to each other, to the ceiling connector 12 and to the service head 14, it is contemplated that other schemes to lock the boom arms 18 in position could be used. For example, other brake assemblies that prevent rotation about the pivot pins 32, 32' could be used. Furthermore, while single pivot pins 32, 32' that connect at top and bottoms thereof to adjacent structures are illustrated, it is contemplated that the pivot pins 32, 32' could be configured as separate top portions and bottom portions.

Furthermore, it is contemplated that the brake systems 104 could be activated and deactivated in any manner. For example, the service head 14 could include a button that is depressed to unlock the brake systems 104 to allow the boom arms 18 to rotate and that locks the brake systems when not depressed. Moreover, it is contemplated that a handle 603 on a shelf 601 connected to poles 600 of the service head or anywhere else on the service head 14 (or item at the end of the boom) could include a capacitance touch system to lock the suspension arm assembly 10 in a selected position once the handle 603 is released such that grasping the handle 603 allows the suspension arm assembly 10 to be moved to a selected position (either immediately or after a pre-programmed delay). A capacitance touch system that releases all brake systems when the handle 603 is grasped and that locks all brake systems when the handle 603 is released is described in U.S. Pat. No. 4,517,632 entitled OPERATING THEATRE LAMP, the entire contents of which are incorporated herein by reference. If the surgical light 14a is used with the suspension arm assembly 10, the handle for the surgical light 14a could include the capacitance touch system. The brake system 104 can include a positive braking system or a clutch system for impeding rotational movement of the boom arms 18.

In the illustrated example, if a capacitance touch brake system is used, there could be a single location that needs to be touched to release the brake systems 104. Alternatively, the capacitance touch brake system could include a two-touch system wherein two spaced locations 605, 607 (see FIGS. 11A and 11B) need to be simultaneously touched to release the brake systems 104 to allow the suspension arm assembly 10 to move. In the two-touch system, both of the locations 605, 607 must be touched at the same time. It is contemplated that there may be single or multiple instances of a first one of the locations 605 and/or single or multiple instances of a second one of the locations 607. FIGS. 11A and 11B illustrate two instances of the first one of the locations 605 and a single instance of the second one of the locations 607. It is contemplated that the locations 605, 607 can be activated by touching a thin plastic element with a wire affixed to an interior side of the element or through direct contact with a metallic element. If direct contact with a metallic element contact is employed, it is contemplated that the metallic element contact would not directly contact any other metals and would not sense any other metallic objects near the metallic element contact (e.g., by using insulating materials such as plastic washers and intermediate materials (for example, a polycarbonate spacer) between two metallic components). It is contemplated that if the wire affixed to a thin plastic element is used that the wire be distanced from other metal objects.

Figure 13A:
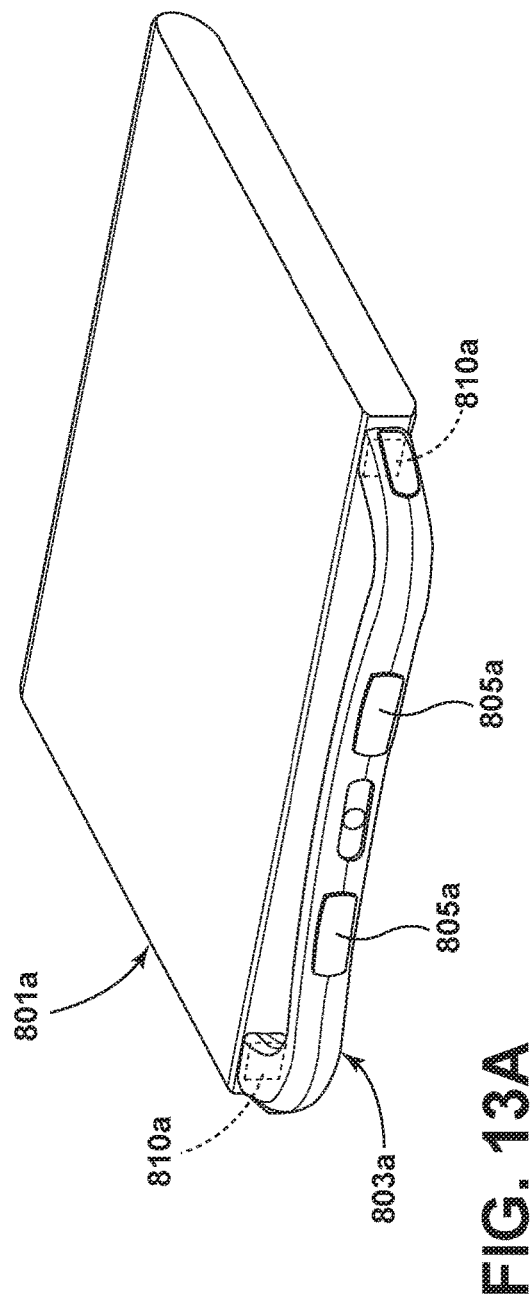
FIG. 13A is a front perspective view of a shelf of the suspension arm assembly of the present invention illustrating a second method of moving the suspension arm assembly.
Figure 13B:
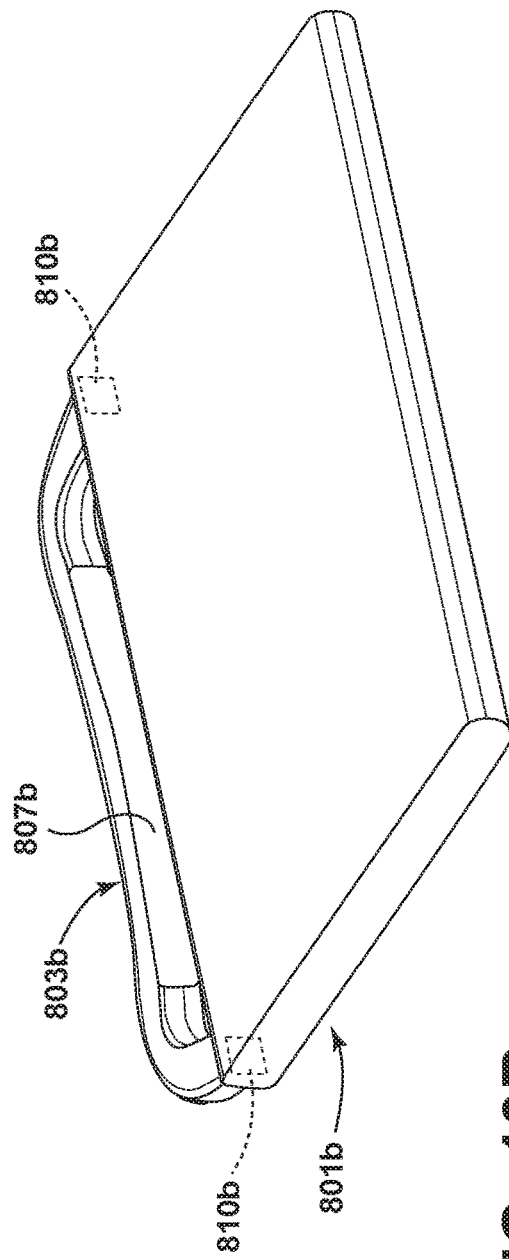
FIG. 13B is a rear perspective view of a shelf of the suspension arm assembly of the present invention illustrating a third method of moving the suspension arm assembly.

Another version of the brake release system has the brake systems 104 releasing based upon both activation of a single capacitance touch sensor (e.g., one of the sensors 805a on the handle 803a of shelf 801a in FIG. 13A or the sensor 807b on the handle 803b of shelf 801b in FIG. 13B) and a force sensor (e.g., the force sensors 810a in FIG. 13A or the sensors 810b in FIG. 13B). The force sensors 810a, 810b can be a single sensor or multiple sensors anywhere on the service head or elsewhere (for example, as shown in FIGS. 13A and 13B). As the force sensor (e.g., a load cell, a strain gauge, a torsion sensor or a pressure sensor) senses a force and the control system senses activation of the capacitance touch sensor, the brake systems 104 release in a predictable manner. It is contemplated that the suspension arm assembly 10 could include indicator light(s) anywhere thereon (e.g., on the handle), with the indicator light(s) indicating that the capacitance touch sensor is sensing contact and that the force sensor is sensing a force. For example, a single light could illuminate when both sensors are activated or multiple lights could be used, one for each sensor. It is contemplated that a force sensor alone could be used to release the brake systems 104 in a predictable manner.

Figure 10:
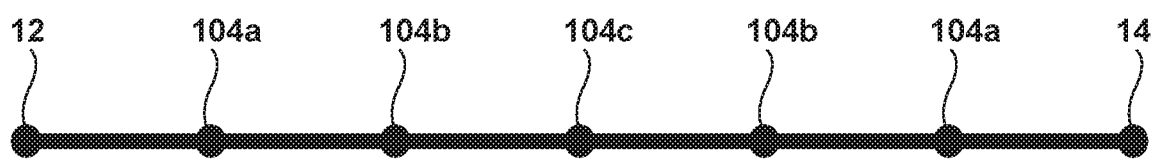
FIG. 10 is a schematic view of the suspension arm assembly of the present invention illustrating a scheme for releasing brake systems of the present invention.

When a brake release system of the suspension arm assembly 10 is activated, it is contemplated that all of the brake systems 104 could be released at the same time to allow all of the booms arms 18 to move. Alternatively, it is contemplated that the brake systems 104 could be released in a particular order. For example, it is contemplated that the brake system 104 of the boom arm 18 closest to the service head 14 and the boom arm 18 connected to the ceiling connector 12 (or other support structure) release first and that after a predetermined time period the brake systems 104 adjacent to the already released brake systems are also released and so on until the brake system 104 (or brake systems) at a central location of the multi-link boom 16 are released. Such a system is illustrated in FIG. 10 wherein the brake systems 104a are released first, followed by the brake systems 104b after a certain time period and finally the brake system 104c after a certain time period. Alternatively, it is contemplated that the brake system 104 at the service head 14 can be released first and then each adjacent brake system 104 moving toward the ceiling connector 12 can be released after a certain time period. For example, when the user engages the brake release system and exerts force to the right, the boom arm 18 closest to the service head 14 releases first and then each adjacent brake system 104 moving toward the ceiling connector 12 is released after a certain time period. It is further contemplated that the brake system 104 at the service head 14 can remain engaged even when all the other brake systems 104a, 104b, 104c, etc. are disengaged (with this feature being activated by a switch (e.g., a button)). It is also contemplated that each of the brake systems 104 could individually be selectively activated (or remain braked) with all remaining brake systems 104, 104a, 104b, 104c, etc. Booming released (or the opposite, with selected brake systems being released with all remaining being braked). For example, if only the brake system 104 of the most proximal joint and the middle joint are disengaged, the multi-link boom 16 would behave like a traditional, two-link boom. In general, it is contemplated that the brake systems 104 of any adjacent boom arms 18 could be selected to remain engaged when other brake systems 104 are disengaged by a user to move the multi-link boom 16. The braking control system can also incorporate position sensors (e.g. encoders, potentiometers) at each joint, and release subsequent joints after joints have articulated a distance, achieved a speed, or the arm has reached a predetermined posture.

Figure 12:
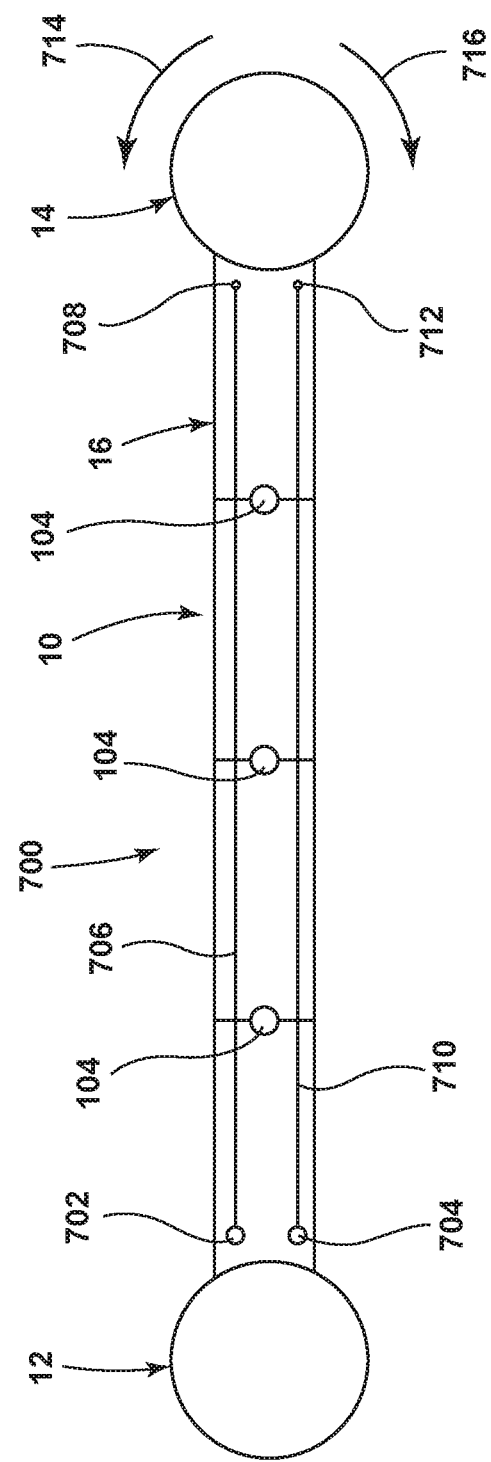
FIG. 12 is a top schematic view of the suspension arm assembly of the present invention having a powered system for moving the boom arms of the multi-link boom of the present invention.

FIG. 12 illustrates schematically a powered movement system 700 for the boom arm assembly 10. The powered movement system 700 includes a first direction powered spool 702 and a second direction powered spool 704. The first direction powered spool 702 and the second direction powered spool 704 are located adjacent the ceiling connector 12 (or other support structure). For example, the first direction powered spool 702 and the second direction powered spool 704 can be located on the ceiling connector 12 or on the boom arm 16 adjacent the ceiling connector 12. The first direction powered spool 702 includes a first link 706 wrapped thereon. The first link 706 can be flexible (e.g., cables or rope) or formed of rigid link sections. The first link 706 is connected to an end of the boom arm assembly 10 (e.g., to the service head 14 or the boom arm 18 adjacent the service head 14) at a first direction end point 708. Likewise, the second direction powered spool 704 includes a second link 710 wrapped thereon. The second link 710 can be flexible (e.g., cables or rope) or formed of rigid link sections. The second link 710 is connected to an end of the boom arm assembly 10 (e.g., to the service head 14 or the boom arm 18 adjacent the service head 14) at a second direction end point 712.

The illustrated powered movement system 700 is configured to assist in moving the service head 14. Under control of a control system, the first direction powered spool 702 and the second direction powered spool 704 can be selectively activated to pull in the first link 706 and the second link 710, respectively. When the first link 706 is pulled, the end of the multi-link boom 16 moves in the first direction 714 as illustrated in FIG. 12. Likewise, when the second link 710 is pulled, the end of the multi-link boom 16 moves in the second direction 716 as illustrated in FIG. 12. In the illustrated example, the brake systems could be modulated or selectively activated to select which joints between adjacent boom arms 18 (and between the boom arms 18 and adjacent ceiling connectors and end device) are allowed to move. In such a system, the joints between adjacent boom arms 18 (and between the boom arms 18 and adjacent ceiling connectors and end device) may contain position sensors and a microprocessor could be used to implement a control system for the powered movement system 700. If the first link 706 and the second link 710 are semi-rigid (e.g. spooled sheet metal), the powered movement system 700 could allow for pushing in addition to pulling forces to be applied.

In the illustrated example, it is contemplated that both the first direction powered spool 702 and the second direction powered spool 704 could be activated to fold the multi-link boom 16 into a fully retracted position. It is further contemplated that in addition to a winding or unwinding of the first direction powered spool 702 and the second direction powered spool 704, tension in the first link 706 and the second link 710 can be controlled (e.g., with pneumatic or hydraulic cylinders). The powered movement system 700 could be designed with the ability to learn movement if a preferred series of steps was desired to reach a desired location. For example, the powered movement system 700 could unlock all brake system 104 along with both the first direction powered spool 702 and the second direction powered spool 704 to map a path of the service head 14 that would be saved as a preset. The powered movement system 700 could also be used to identify areas of the room where the boom arm assembly 10 would not be allowed to travel to prevent the boom arm assembly 10 from hitting walls or colliding with other ceiling mounted equipment. It is contemplated that the boom arm assembly 10 could require the user to engage and maintain the powered movement system 700 or that the boom arm assembly 10 could move under control solely of the powered movement system 700. It is also contemplated that instead of powered spools, other actuators (e.g., hydraulic and/or pneumatic linear actuators) could be used or a single spool could be used for pulling on a pair of links.

The illustrated suspension arm assembly 10 having the multi-link boom 16 allows for easy movement of the service head 14 (or other device located on the end of the multi-link boom 16), compact storage and easy routing of at least one conduit. Since the multi-link boom 16 include many boom arms 18, the multi-link boom 16 can be easily adjusted around other objects in a room and can be folded to be in a compact configuration. Furthermore, since the boom arms 18 of the multi-link boom 16 are horizontally aligned, the suspension arm assembly 10 has a short vertical profile and thereby takes up less room than prior art suspension arm assemblies. While each arm of the multi-link boom is illustrated as being substantially identical, it is contemplated that the arm closest to the ceiling attachment member could be the largest (e.g, be the longest and/or have the greatest thickness) and the end arm could be the smallest (e.g., be the shortest and/or have the slightest thickness), with each arm having a different size (e.g., length and/or thickness) or some adjacent arms have the same size (e.g., length and/or thickness).

The illustrated suspension arm assembly 10 could also include a force sensor 900 (e.g., a load cell, a strain gauge, a torsion sensor or a pressure sensor) adjacent the ceiling connector 12 (see FIG. 1) for sensing a weight of the remainder of the suspension arm assembly 10 (i.e., the weight of the suspension arm assembly 10 distal to the sensor 900 or moving away from the ceiling connector 12). If the weight of the remainder of the suspension arm assembly 10 is too great, an indicator 901 can be illuminated to indicate that more weight should not be added to the suspension arm assembly 10 and that some weight should be removed. Weight can be lessened, for example, by removing elements of the service head 14 (or other item at the end of the multi-link boom 16) or shortening the multi-link boom 16.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A suspension arm assembly comprising:
   at least three horizontally aligned members relatively rotatable about each other, each adjacent pair of the at least three horizontally aligned members being connected to each other by a joint, each of the at least three horizontally aligned members defining a load bearing periphery;
   a boom connecting assembly rotatably connected to one of the at least three horizontally aligned members;
   at least one conduit extending along the at least three horizontally aligned members and down through a central portion of the boom connecting assembly, the at least one conduit not being located within the load bearing periphery of each of the at least three horizontally aligned members, wherein the at least one conduit is positioned vertically outward of the load bearing periphery of each of the at least three horizontally aligned members as the at least one conduit extends along the at least three horizontally aligned members;
   a brake system comprising a brake at each joint for selectively preventing movement of respective adjacent ones of the at least three horizontally aligned members about the joint, wherein the brake system is configured to require activation of at least two sensors to release the brake at each joint; and
   at least one boom shell about the at least three horizontally aligned members.

2. The suspension arm assembly of claim 1, wherein:
   the at least one conduit is routed horizontally and not vertically between each adjacent pair of the at least three horizontally aligned members.

3. The suspension arm assembly of claim 1,
   wherein each of the at least three horizontally aligned members includes at least one conduit routing housing located between the load bearing periphery and the at least one boom shell, the at least one conduit routing housing of each of the at least three horizontally aligned members having the at least one conduit being routed therethrough.

4. The suspension arm assembly of claim 1, wherein:
   each of the at least three horizontally aligned members includes at least one conduit routing housing located outside of the load bearing periphery and having the at least one conduit therein.

5. The suspension arm assembly of claim 1, wherein:
   each of the at least three horizontally aligned members includes a pivot pin for connecting to an adjacent one of the at least three horizontally aligned members, each pivot pin engaging a respective one of the brakes of the brake system for selectively preventing rotation of the adjacent one of the at least three horizontally aligned members about the pivot pin.

6. The suspension arm assembly of claim 5, wherein:
   each of the at least three horizontally aligned members includes a removable C-shaped flange for selectively locking the pivot pin in position on the at least three horizontally aligned members.

7. The suspension arm assembly of claim 1, wherein:
   the at least two sensors comprise at least two spaced capacitance touch sensors.

8. The suspension arm assembly of claim 1, wherein:
   the at least three horizontally aligned members are hollow and have a substantially rectangular cross-sectional shape.

9. The suspension arm assembly of claim 1, wherein:
   at least two of the at least three horizontally aligned members are substantially identical.

10. The suspension arm assembly of claim 1, further including:
    a powered system for selectively causing rotations of at least two of the at least three horizontally aligned members about each other.

11. The suspension arm assembly of claim 1, wherein:
    the brake system is configured for sequential release of the brakes of the brake system.

12. The suspension arm assembly of claim 1, wherein the at least one conduit extends above an uppermost portion of the load bearing periphery of each of the at least three horizontally aligned members as the at least one conduit extends along each of the at least three horizontally aligned members.

13. The suspension arm assembly of claim 1, comprising a service head that is connected to the at least three horizontally aligned members via the boom connecting assembly.

14. The suspension arm assembly of claim 1, wherein an upper portion of the boom connecting assembly is configured to funnel the at least one conduit into the central portion of the boom connecting assembly.

15. A medical suspension arm assembly comprising:
at least three horizontally aligned members relatively rotatable about each other, each adjacent pair of the at least three horizontally aligned members being connected to each other by a joint, each of the at least three horizontally aligned members defining a load bearing periphery;
a boom connecting assembly rotatably connected to one of the at least three horizontally aligned members;
at least one conduit extending along a ceiling attachment member, the at least three horizontally aligned members, and down through a central portion of the boom connecting assembly, the at least one conduit not being located within the load bearing periphery of each of the at least three horizontally aligned members, wherein the at least one conduit is positioned vertically outward of the load bearing periphery of each of the at least three horizontally aligned members as the at least one conduit extends along the at least three horizontally aligned members;
a brake system comprising a brake at each joint for selectively preventing movement of respective adjacent ones of the at least three horizontally aligned members about the joint, wherein the brake system is configured to require activation of at least two sensors to release the brake at each joint; and
at least one boom shell about the at least three horizontally aligned members.

16. The medical suspension arm assembly of claim 15, wherein:
the at least one conduit is routed horizontally and not vertically between each adjacent pair of the at least three horizontally aligned members.

17. The medical suspension arm assembly of claim 15, wherein each of the at least three horizontally aligned members includes at least one conduit routing housing located between the load bearing periphery and the at least one boom shell, the at least one conduit routing housing of each of the at least three horizontally aligned members having the at least one conduit being routed therethrough.

18. The medical suspension arm assembly of claim 15, wherein:
each of the at least three horizontally aligned members includes at least one conduit routing housing located outside of the load bearing periphery and having the at least one conduit therein.

19. The medical suspension arm assembly of claim 15, wherein:
each of the at least three horizontally aligned members includes a pivot pin located between each adjacent pair of the at least three horizontally aligned members, each pivot pin engaging a respective one of the brakes of the brake system for selectively preventing rotation of the adjacent pair of the at least three horizontally aligned members about the pivot pin.

20. The medical suspension arm assembly of claim 19, wherein:
each of the at least three horizontally aligned members includes a removable C-shaped arm for selectively locking the pivot pin in position on the at least three horizontally aligned members.

21. The medical suspension arm assembly of claim 15, wherein:
the at least three horizontally aligned members are hollow and have a substantially rectangular cross-sectional shape.

22. The medical suspension arm assembly of claim 15, comprising a medical device supported by the at least three horizontally aligned members and the boom connecting assembly for providing medical services or information, wherein:
the medical device comprises a service head.

23. The medical suspension arm assembly of claim 15, comprising a medical device supported by the at least three horizontally aligned members and the boom connecting assembly for providing medical services or information, wherein:
the medical device comprises a surgical light.

24. The medical suspension arm assembly of claim 15, wherein:
at least two of the at least three horizontally aligned members are substantially identical.

25. A medical suspension arm assembly comprising:
an attachment member for connecting the medical suspension arm assembly to a support structure;
at least three horizontally aligned members relatively rotatable about each other, each adjacent pair of the at least three horizontally aligned members being connected to each other by a joint;
a boom connecting assembly rotatably connected to one of the at least three horizontally aligned members;
a medical device supported by the at least three horizontally aligned members and the boom connecting assembly for providing medical services or information;
at least one conduit extending along the attachment member, the at least three horizontally aligned members, and down through a central portion of the boom connecting assembly to the medical device, the at least one conduit being routed horizontally and not vertically between each adjacent pair of the at least three horizontally aligned members, wherein the at least one conduit is positioned vertically outward of the load bearing periphery of each of the at least three horizontally aligned members as the at least one conduit extends along the at least three horizontally aligned members; and
a brake system comprising a brake at each joint for selectively preventing movement of respective adjacent ones of the at least three horizontally aligned members about the joint, wherein the brake system is configured to require activation of at least two sensors to release the brake at each joint, wherein the at least two sensors comprise at least two spaced capacitance touch sensors.

26. The medical suspension arm assembly of claim 25, wherein:
at least two of the at least three horizontally aligned members are substantially identical.

27. The medical suspension arm assembly of claim 25, wherein:
at least one of the at least three horizontally aligned members has an arm horizontal length smaller than 25% of a total horizontal length of all of the at least three horizontally aligned members.

28. A medical suspension arm assembly comprising:
an attachment member for connecting the medical suspension arm assembly to a support structure;
at least three horizontally aligned members relatively rotatable about each other, each adjacent pair of the at least three horizontally aligned members being connected to each other by a joint;
a medical device for providing medical services or information;

at least one conduit extending along the attachment member, the at least three horizontally aligned members and to the medical device, wherein the at least one conduit is positioned vertically outward of the load bearing periphery of each of the at least three horizontally aligned members as the at least one conduit extends along the at least three horizontally aligned members; and a brake system comprises a brake at each joint for selectively preventing movement of respective adjacent ones of the at least three horizontally aligned members about the joint, with each brake being aligned with a rotational axis of the joint and located outside a periphery of the respective adjacent ones of the at least three horizontally aligned members along the rotational axis, wherein each brake is located outside of an outermost side of the respective adjacent ones of the at least three horizontally aligned members in a direction of the rotational axis of the joint, and wherein the brake system is configured to require activation of at least two sensors to release the brake at each joint.

29. The medical suspension arm assembly of claim 28, wherein:
the at least two sensors comprise at least two spaced capacitance touch sensors.

30. The medical suspension arm assembly of claim 28, wherein:
the brake system is configured to sequentially release each brake according to an order of each brake along the medical suspension arm assembly.

31. The medical suspension arm assembly of claim 28, wherein:
each brake is released when at least two spaced capacitance touch sensors are touched along with a force sensor sensing a movement force.

32. A method of using a suspension arm assembly comprising:
repositioning an end of the suspension arm assembly, the suspension arm assembly comprising at least three horizontally aligned members rotatably connected to each other, each adjacent pair of the at least three horizontally aligned members being connected to each other by a joint, a boom connecting assembly rotatably connected to one of the at least three horizontally aligned members, and at least one conduit extending along the at least three horizontally aligned members and down through a central portion of the boom connecting assembly, each of the at least three horizontally aligned members defining a load bearing periphery, and the at least one conduit not being located within the load bearing periphery of each of the at least three horizontally aligned members, wherein the at least one conduit is positioned vertically outward of the load bearing periphery of each of the at least three horizontally aligned members as the at least one conduit extends along the at least three horizontally aligned members wherein the suspension arm assembly comprises a brake system comprising a brake at each joint for selectively preventing movement of respective adjacent ones of the at least three horizontally aligned members about the joint, wherein the brake system is configured to require activation of at least two sensors to release the brake at each joint, and wherein an upper portion of the boom connecting assembly is configured to funnel the at least one conduit into the central portion of the boom connecting assembly.

33. The method of using the suspension arm assembly of claim 32, further including:
sequentially releasing the brakes of the brake system.

34. The method of using the suspension arm assembly of claim 32, further including releasing at least one but not all of the brakes to reduce degrees of freedom of movement of the suspension arm assembly.

* * * * *